(12) United States Patent
Schneider et al.

(10) Patent No.: US 11,505,511 B2
(45) Date of Patent: Nov. 22, 2022

(54) PROCESS FOR PREPARING IMPROVED 3,4-DIMETHYL-1H-PYRAZOLE PHOSPHATE FORMULATIONS

(71) Applicant: BASF SE, Ludwigshafen am Rhein (DE)

(72) Inventors: Karl-Heinrich Schneider, Limburgerhof (DE); Gregor Pasda, Limburgerhof (DE); Wolfram Zerulla, Limburgerhof (DE); Markus Schmid, Limburgerhof (DE); Daniella Lohe, Limburgerhof (DE); Alexander Wissemeier, Limburgerhof (DE); Maarten Staal, Limburgerhof (DE); Barbara Nave, Limburgerhof (DE); Claudia Klodwig, Limburgerhof (DE)

(73) Assignee: BASF SE, Ludwigshafen am Rhein (DE)

( * ) Notice: Subject to any disclaimer, the term of this patent is extended or adjusted under 35 U.S.C. 154(b) by 128 days.

(21) Appl. No.: 16/634,262

(22) PCT Filed: Aug. 17, 2018

(86) PCT No.: PCT/IB2018/056214
§ 371 (c)(1),
(2) Date: Jan. 27, 2020

(87) PCT Pub. No.: WO2019/035069
PCT Pub. Date: Feb. 21, 2019

(65) Prior Publication Data
US 2020/0165173 A1    May 28, 2020

(30) Foreign Application Priority Data
Aug. 18, 2017   (WO) ............... PCT/EP2017/070959

(51) Int. Cl.
*C05G 3/90*   (2020.01)
*A01C 21/00*  (2006.01)
*C09K 15/16*  (2006.01)
*C05C 9/00*   (2006.01)

(52) U.S. Cl.
CPC ........... *C05G 3/90* (2020.02); *A01C 21/00* (2013.01); *C05C 9/005* (2013.01); *C09K 15/16* (2013.01)

(58) Field of Classification Search
None
See application file for complete search history.

(56) References Cited

U.S. PATENT DOCUMENTS

| | | | |
|---|---|---|---|
| 3,635,690 A * | 1/1972 | Griffith | ........ C05G 3/90 71/1 |
| 6,802,882 B2 | 10/2004 | Barth et al. | |
| 10,173,940 B2 | 1/2019 | Tironi Gallardo | |
| 2014/0360239 A1* | 12/2014 | Kleine-Kleffmann | ........ C07C 273/02 71/28 |
| 2017/0253535 A1* | 9/2017 | Gabrielson | ........ C05G 3/90 |
| 2017/0362140 A1* | 12/2017 | Sculthorpe | ........ C05G 5/30 |
| 2018/0016199 A1* | 1/2018 | Nave | ........ A01N 43/58 |
| 2018/0249626 A1* | 9/2018 | Zerulla | ........ A01C 21/00 |
| 2018/0273557 A1 | 9/2018 | Lang et al. | |
| 2019/0048260 A1* | 2/2019 | Waliwitiya | ........ C09K 15/30 |
| 2019/0055169 A1 | 2/2019 | Peters | |
| 2019/0092704 A1* | 3/2019 | Nave | ........ C05F 3/00 |
| 2019/0112241 A1 | 4/2019 | Staal et al. | |
| 2019/0276376 A1 | 9/2019 | Schneider et al. | |
| 2019/0359538 A1 | 11/2019 | Nils | |
| 2020/0002609 A1 | 1/2020 | Mainwaring et al. | |

FOREIGN PATENT DOCUMENTS

| | | | |
|---|---|---|---|
| CN | 105452199 A | 3/2016 | |
| DE | 10164104 C 1 * | 6/2003 | ........ C05G 3/08 |
| DE | 10164104 C1 | 6/2003 | |
| DE | 202014003261 U1 | 5/2014 | |
| EP | 1120388 A1 | 8/2001 | |
| EP | 1323695 A2 | 7/2003 | |
| EP | 1340738 A1 | 9/2003 | |
| WO | 9805607 A2 | 2/1998 | |
| WO | 2015081116 A1 | 6/2015 | |
| WO | 2016113727 A1 | 7/2016 | |
| WO | 2016207210 A1 | 12/2016 | |
| WO | 2017198693 A1 | 11/2017 | |
| WO | 2018116046 A1 | 6/2018 | |
| WO | 2018141708 A1 | 8/2018 | |
| WO | 2018158675 A1 | 9/2018 | |
| WO | 2019012377 A1 | 1/2019 | |
| WO | 2019012378 A1 | 1/2019 | |
| WO | 2019012379 A1 | 1/2019 | |
| WO | 2019012380 A1 | 1/2019 | |
| WO | 2019012381 A1 | 1/2019 | |
| WO | 2019012382 A1 | 1/2019 | |
| WO | 2019012383 A1 | 1/2019 | |

OTHER PUBLICATIONS

International Search Report for International Application No. PCT/IB2018/056214, dated Dec. 5, 2018, 4 pages.
Written Opinion of the International Searching Authority for International Application No. PCT/IB2018/056214, dated Dec. 5, 2018, 4 pages.
Supplementary European Search Report for corresponding EP Patent Application No. 18845547, dated Apr. 15, 2021, 13 pages.

* cited by examiner

*Primary Examiner* — Wayne A Langel
(74) *Attorney, Agent, or Firm* — Armstrong Teasdale LLP

(57) ABSTRACT

The present invention relates to a process for preparing a formulation F for reducing nitrification. The present invention also relates to a formulation F obtainable by the process of the invention. Furthermore, the present invention relates to a process of preparing a fertilizer-nitrification inhibitor mixture, and to a fertilizer-nitrification inhibitor mixture obtainable by this process. Moreover, the present invention relates to a method of fertilizing agricultural soil.

18 Claims, No Drawings

PROCESS FOR PREPARING IMPROVED 3,4-DIMETHYL-1H-PYRAZOLE PHOSPHATE FORMULATIONS

CROSS-REFERENCE TO RELATED APPLICATIONS

This application is a U.S. National Phase Application of International Patent Application No. PCT/IB2018/056214, filed Aug. 17, 2018, which claims the benefit of priority to International Patent Application No. PCT/EP2017/070959, filed Aug. 18, 2017, the contents of which are hereby expressly incorporated by reference in their entirety.

The present invention relates to a process for preparing a formulation F for reducing nitrification comprising 3,4-dimethyl-1H-pyrazole phosphate by mixing a solution S comprising 3,4-dimethyl-1H-pyrazole phosphate and 3,4-dimethyl-1H-pyrazole with a suitable amount of water and phosphoric acid. The present invention also relates to a formulation F obtainable by the process of the invention. Furthermore, the present invention relates to a process of preparing a fertilizer-nitrification inhibitor mixture by treating at least one fertilizer with a formulation F according to the invention, and to a fertilizer-nitrification inhibitor mixture obtainable by this process. Moreover, the present invention relates to a method of fertilizing agricultural soil by applying at least one fertilizer and a formulation F according to the invention to said soil, or by applying a fertilizer-nitrification inhibitor mixture according to the invention to said soil.

The present invention further relates to a solution S comprising 3,4-dimethyl-1H-pyrazole phosphate and 3,4-dimethyl-1H-pyrazole, a process of preparing said solution, and to a solution S obtainable by said process.

Nitrification of nitrogen containing compounds is a phenomenon that reduces the efficiency of fertilization of soil with nitrogen containing compounds.

Through nitrification, N-containing compounds are decomposed by bacteria. Thereby, the nitrogen contained therein is oxidized and is no longer available for take-up by the crops.

One common approach to reduce nitrification is to apply nitrification inhibitors to the soil. In particular, fertilizers may be treated with nitrification inhibitors to reduce nitrification, when the fertilizer is applied to the soil.

EP 1 120 388 A1 discloses the use of pyrazoles like 3,4-dimethylpyrazol (DMP) or 3,4-dimethylpyrazole phosphate as nitrification inhibitors.

EP 1 323 695 A2 discloses a process of preparing a fertilizer composition comprising a pyrazole based nitrification inhibitor by treating the fertilizer with a solution of the nitrification inhibitor at elevated temperatures.

EP 1 340 738 A1 discloses a process of preparing a fertilizer composition comprising a nitrification inhibitor by treating the fertilizer with a solution of the nitrification inhibitor in a special mixer.

However, the formulations for treating the fertilizer with the nitrification inhibitor described in the prior art have disadvantages. In particular, it is desired that the formulations are also suitable for use at lower temperatures. However, if formulations comprising 3,4-dimethyl-1H-pyrazole phosphate as nitrification inhibitor are used, crystallization of the nitrification inhibitor at lower temperatures causes problems. Accordingly, there is a need to improve the cold stability of formulations comprising 3,4-dimethyl-1H-pyrazole phosphate and to provide a convenient process for preparing stable formulations comprising 3,4-dimethyl-1H-pyrazole phosphate.

In view of the above, it was an object of the present invention to provide a process for preparing a cold stable formulation comprising 3,4-dimethyl-1H-pyrazole phosphate. In this regard, it was also an object to provide a process, which can conveniently be carried out starting from a storage stable precursor and without having to apply heat.

Furthermore, it was an object of the present invention to provide a formulation comprising 3,4-dimethyl-1H-pyrazole phosphate with advantageous properties in terms of the cold stability, and which is suitable for treating at least one fertilizer to obtain a fertilizer-nitrification inhibitor mixture comprising at least one fertilizer and 3,4-dimethyl-1-H-pyrazole phosphate. In this regard, it was also an object of the present invention to provide a formulation comprising 3,4-dimethyl-1H-pyrazole phosphate, which is suitable for treating at least one fertilizer, while the problem of caking, i.e. clogging, due to the treatment with the formulation is reduced.

Furthermore, it was an object to provide a precursor of the formulation comprising 3,4-dimethyl-1H-pyrazole, wherein said precursor can be easily converted into the formulation comprising 3,4-dimethyl-1H-pyrazole, and which is storage stable.

The above objects were achieved by the present invention.

In one embodiment, the present invention relates to a process for preparing a formulation F for reducing nitrification, said formulation F comprising
  from 10 to 50% by weight of 3,4-dimethyl-1H-pyrazole phosphate,
  from 10 to 50% by weight of phosphoric acid, and
  from 10 to 60% by weight of water,
  in each case based on the total weight of formulation F,
    wherein the process comprises the step of mixing a solution S comprising
  from 10 to 22% by weight of 3,4-dimethyl-1H-pyrazole phosphate,
  from 58 to 70% by weight of 3,4-dimethyl-1H-pyrazole, and
  from 10 to 30% by weight of water,
  in each case based on the total weight of the solution S, with water and phosphoric acid.

It has been found that solution S is a valuable precursor for preparing the formulation F because solution S is storage stable, while it still contains a high amount of active ingredient in the form of 3,4-dimethyl-1H-pyrazole phosphate (DMPP) and 3,4-dimethyl-1H-pyrazole (DMP). Furthermore, the process of the invention provides the formulation F with advantageous properties in terms of the cold stability. Moreover, the process is advantageous because it is not required to apply heat in order to obtain formulation F in the form of a solution.

In another embodiment, the present invention relates to a formulation F comprising
  from 10 to 50% by weight of 3,4-dimethyl-1H-pyrazole phosphate,
  from 30 to 50% by weight of phosphoric acid, and
  from 10 to 60% by weight of water,
  in each case based on the total weight of formulation F, which is obtainable by the process according to the invention.

Formulation F obtained according the process of the present invention exhibits advantageous properties in terms of the cold stability in comparison to a formulation obtained by dissolving crystalline DMPP.

In another embodiment, the present invention relates to a process for preparing a fertilizer-nitrification inhibitor mixture comprising at least one fertilizer and 3,4-dimethyl-1H-pyrazole phosphate by treating at least one fertilizer with a formulation F obtained according to the present invention.

The process is advantageous because the formulation F can be applied to a fertilizer, while the problem of caking, i.e. clogging, due to the treatment of the formulation can be reduced.

In yet another embodiment, the present invention relates to a fertilizer-nitrification inhibitor mixture obtainable by the process for preparing a fertilizer-nitrification inhibitor mixture according to the invention.

In yet another embodiment, the present invention relates to a method of fertilizing agricultural soil by applying at least one fertilizer and a formulation F according to the invention to said soil, or by applying a fertilizer-nitrification inhibitor mixture according to the invention to said soil.

In yet another embodiment, the present invention relates to the use of a formulation F according to the invention for reducing nitrification.

In another embodiment, the present invention relates to a solution S comprising
    from 10 to 22% by weight of 3,4-dimethyl-1H-pyrazole phosphate,
    from 58 to 70% by weight of 3,4-dimethyl-1H-pyrazole, and
    from 10 to 30% by weight of water,
    in each case based on the total weight of the solution S.

As discussed above, the solution S is a valuable precursor for the preparation of the formulation F according to the process of the invention.

In another embodiment, the present invention therefore also relates to the use of solution S as defined herein for preparing the formulation F according to the present invention.

In yet another embodiment, the present invention relates to a process for preparing the solution S as defined above by adding 3,4-dimethyl-1H-pyrazole to a mixture comprising phosphoric acid and water at a temperature of from 30° C. to 80° C., wherein
    3,4-dimethyl-1H-pyrazole is provided in an amount of from 63 to 81% by weight,
    phosphoric acid is provided in an amount of from 5 to 11% by weight, and
    water is provided in an amount of from 10 to 30% by weight,
    in each case based on the total weight of the resulting solution S.

In yet another embodiment, the present invention relates to a solution S obtainable by the process defined above.

The following definitions are relevant in the context of the present invention.

The term "nitrification inhibitor" is to be understood as a chemical substance which slows down or stops the nitrification process. Nitrification inhibitors accordingly retard the natural transformation of ammonium into nitrate, by inhibiting the activity of bacteria such as Nitrosomonas spp. The term "nitrification" as used herein is to be understood as the biological oxidation of ammonia ($NH_3$) or ammonium ($NH_4^+$) with oxygen into nitrite ($NO_2$) followed by the oxidation of these nitrites into nitrates ($NO_3^-$) by microorganisms. Besides nitrate ($NO_3^-$) nitrous oxide is also produced through nitrification. Nitrification is an important step in the nitrogen cycle in soil. The inhibition of nitrification may thus also reduce $N_2O$ losses. The term nitrification inhibitor is considered equivalent to the use of such a compound for reducing nitrification. The term "reducing nitrification" or "reduction of nitrification" as used herein refers to a slowing down or stopping of nitrification processes, e.g. by retarding or eliminating the natural transformation of ammonium into nitrate. Such reduction may be a complete or partial elimination of nitrification at the plant or locus where the inhibitor or composition comprising said inhibitor is applied. For example, a partial elimination may result in a residual nitrification on or in the plant, or in or on the soil or soil substituents where a plant grows or is intended to grow of about 90% to 1%, e.g. 90%, 85%, 80%, 70%, 60%, 50%, 40%, 30%, 20%, 10% or less than 10%, e.g. 5% or less than 5% in comparison to a control situation where the nitrification inhibitor is not used. In certain embodiments, a partial elimination may result in a residual nitrification on or in the plant or in or on the soil or soil substituents where a plant grows or is intended to grow of below 1%, e.g. at 0.5%, 0.1% or less in comparison to a control situation where the nitrification inhibitor is not used.

In the context of the present invention, 3,4-dimethyl-1H-pyrazole acts as nitrification inhibitor. Formulation F according to the present invention contains 3,4-dimethyl-1H-pyrazole phosphate instead of 3,4-dimethyl-1H-pyrazole because the phosphate salt has a reduced volatility. However, within the soil, the 3,4-dimethyl-1H-pyrazole is the active species. Therefore, the formulation F according to the present invention is suitable for reducing nitrification. Preferably, the formulation F is a solution, i.e. comprises the 3,4-dimethyl-1H-pyrazole in dissolved form.

The term "formulation F for reducing nitrification" as used herein refers to a formulation, preferably a solution, as defined herein, which is suitable, e.g. comprises effective concentrations and amounts of a nitrification inhibitor, in particular 3,4-dimethyl-1H-pyrazole phosphate, for reducing nitrification in any context or environment in which nitrification may occur. In one embodiment, the nitrification may be reduced in or on or at the locus of a plant. Typically, the nitrification may be reduced in the root zone of a plant. However, the area in which such reduction of nitrification may occur is not limited to the plants and their environment, but may also include any other habitat of nitrifying bacteria or any site at which nitrifying enzymatic activities can be found or can function in a general manner, e.g. sewage plants, biogas plants, animal effluents from productive livestock, e.g. cows, pigs etc.. "Effective amounts" or "effective concentrations" of nitrification inhibitors as defined herein may be determined according to suitable in vitro and in vivo testings known to the skilled person. These amounts and concentrations may be adjusted to the locus, plant, soil, climate conditions or any other suitable parameter, which may have an influence on nitrification processes.

Formulation F further comprises phosphoric acid. The term "phosphoric acid" as used herein preferably refers to orthophosphoric acid, i.e. $H_3PO_4$, which is typically used in the form of an aqueous solution comprising 85% by weight of orthophosphoric acid.

The formulations F exhibit advantageous properties in terms of the cold stability. The term "cold stability" as used herein refers to the stability of the formulation F in terms of the crystallization of 3,4-dimethyl-1H-pyrazole phosphate (DMPP) at lower temperatures. The cold stability is considered to be good, if crystallization only occurs below 20° C. The cold stability may be tested as follows. Samples of the formulation F1 are put on storage at different temperatures for 1 week. Then traces of DMPP seeding crystals are added and the mixture is stored for another week at the same temperature. Then, the samples are visually investigated for crystals. A high cold stability in combination with a high concentration of DMPP of the formulation F is advantageous because the formulation should advantageously be in the form of a solution, so that it can be easily applied to the soil or used for treating a fertilizer. In terms of the treatment of a fertilizer, it is at the same time required that the DMPP concentration is as high as possible in order to reduce caking, i.e. clogging. Therefore, cold stability is of particular relevance in this connection.

As used herein, the term "fertilizer" is to be understood as chemical compounds applied to promote plant and fruit growth. Fertilizers are typically applied either through the soil (for uptake by plant roots), through soil substituents (also for uptake by plant roots), or by foliar feeding (for uptake through leaves). The term also includes mixtures of one or more different types of fertilizers as mentioned below. The term "fertilizers" can be subdivided into several categories including: a) organic fertilizers (composed of decayed plant/animal matter), b) inorganic fertilizers (composed of chemicals and minerals) and c) urea-containing fertilizers.

Organic fertilizers include manure, e.g. liquid manure, semi-liquid manure, biogas manure, stable manure or straw manure, slurry, worm castings, peat, seaweed, compost, sewage, and guano. Green manure crops are also regularly grown to add nutrients (especially nitrogen) to the soil. Manufactured organic fertilizers include compost, blood meal, bone meal and seaweed extracts. Further examples are enzyme digested proteins, fish meal, and feather meal. The decomposing crop residue from prior years is another source of fertility. In addition, naturally occurring minerals such as mine rock phosphate, sulfate of potash and limestone are also considered inorganic fertilizers.

Inorganic fertilizers are usually manufactured through chemical processes (such as the Haber process), also using naturally occurring deposits, while chemically altering them (e.g. concentrated triple superphosphate). Naturally occurring inorganic fertilizers include Chilean sodium nitrate, mine rock phosphate, limestone, and raw potash fertilizers.

Urea-containing fertilizer may, in specific embodiments, be urea, formaldehyde urea, anhydrous ammonium, urea ammonium nitrate (UAN) solution, urea sulfur, urea based NPK-fertilizers, or urea ammonium sulfate. Also envisaged is the use of urea as fertilizer. In case urea-containing fertilizers or urea are used or provided, it is particularly preferred that urease inhibitors as defined herein above may be added or additionally be present, or be used at the same time or in connection with the urea-containing fertilizers.

Fertilizers may be provided in any suitable form, e.g. as solid coated or uncoated granules, in liquid or semi-liquid form, as sprayable fertilizer, or via fertigation etc. It is to be understood that various combinations of fertilizers may be used.

In particularly preferred embodiments, the fertilizer is an ammonium-containing fertilizer.

The term "treating a fertilizer with a Formulation F" refers to a treatment of a fertilizer with the Formulation F in order to apply the nitrification inhibitor, i.e. DMPP, to the fertilizer. Suitable treatment processes are known to the skilled person and may include, for instance, dressing, coating, pelleting, dusting or soaking. In a specific embodiment, the treatment may be a coating of fertilizers with the formulation F. The treatment may be based on the use of granulation methods as known to the skilled person, e.g. fluidized bed granulation. After treatment, a "fertilizer-nitrification inhibitor mixture" is obtained, which is preferably in the form of a fertilizer being coated with the nitrification inhibitor, i.e. DMPP.

Preferred embodiments regarding the present invention are defined hereinafter. The preferred embodiments are preferred alone as well as in combination with each other.

As indicated above, the present invention relates in one embodiment to a process for preparing a formulation F for reducing nitrification, said formulation F comprising
from 10 to 50% by weight of 3,4-dimethyl-1H-pyrazole phosphate,
from 10 to 50% by weight of phosphoric acid, and
from 10 to 60% by weight of water,
in each case based on the total weight of formulation F, wherein the process comprises the step of mixing a solution S comprising
from 10 to 22% by weight of 3,4-dimethyl-1H-pyrazole phosphate,
from 58 to 70% by weight of 3,4-dimethyl-1H-pyrazole, and
from 10 to 30% by weight of water,
in each case based on the total weight of the solution S, with water and phosphoric acid.

It is to be understood that the solution S is mixed with suitable amounts of water and phosphoric acid, so as to obtain the desired weight percent amounts of the ingredients of formulation F. Preferably, the solution S is added to a mixture comprising water and phosphoric acid, in order to obtain formulation F.

The formulation F prepared according to the process of the present invention comprises
from 10 to 50% by weight of 3,4-dimethyl-1H-pyrazole phosphate,
from 10 to 50% by weight of phosphoric acid, and
from 10 to 60% by weight of water,
in each case based on the total weight of formulation F.

In one preferred embodiment, the formulation F comprises 3,4-dimethyl-1H-pyrazole phosphate (DMPP) in an amount of from 25 to 45% by weight, more preferably in an amount of from 28 to 42% by weight, most preferably in an amount of from 30 to 40% by weight, particularly preferably in an amount of from 32 to 38% by weight, particularly more preferably in an amount of from 33 to 37% by weight, particularly most preferably in an amount of from 34 to 36% by weight, in each case based on the total weight of the formulation F.

In another preferred embodiment, the formulation F comprises phosphoric acid in an amount of from 15 to 45% by weight, more preferably in an amount of from 25 to 45% by weight, most preferably in an amount of from 30 to 45% by weight, particularly preferably in an amount of from 35 to 45% by weight, particularly more preferably in an amount of from 36 to 42% by weight, particularly most preferably in an amount of from 37 to 39% by weight, in each case based on the total weight of the formulation F.

In another preferred embodiment, the formulation F comprises water in an amount of from 20 to 50% by weight, more preferably from 20 to 40% by weight, most preferably from 27 to 29% by weight, in each case based on the total weight of the formulation F.

In a preferred embodiment, the formulation F comprises
from 30 to 40% by weight of 3,4-dimethyl-1H-pyrazole phosphate,
from 35 to 45% by weight of phosphoric acid, and
from 20 to 40% by weight of water,
in each case based on the total weight of formulation F.

In a more preferred embodiment, the formulation F comprises
- from 34 to 36% by weight of 3,4-dimethyl-1H-pyrazole phosphate,
- from 37 to 39% by weight of phosphoric acid, and
- from 27 to 29% by weight of water,
in each case based on the total weight of formulation F.

In an even more preferred embodiment, the formulation F comprises
- about 35% by weight of 3,4-dimethyl-1H-pyrazole phosphate,
- about 38% by weight of phosphoric acid, and
- about 28% by weight of water,
in each case based on the total weight of formulation F.

In connection with the above embodiment, the term "about" refers to a variance of ±0.5, preferably ±0.2.

The solution S, which is used as a precursor for preparing the formulation F in the process of the present invention, comprises
- from 10 to 22% by weight of 3,4-dimethyl-1H-pyrazole phosphate,
- from 58 to 70% by weight of 3,4-dimethyl-1H-pyrazole, and
- from 10 to 30% by weight of water,
in each case based on the total weight of the solution S, In one preferred embodiment, the solution S comprises 3,4-dimehtyl-1H-pyrazole phosphate (DMPP) in an amount of from 12 to 20% by weight, preferably from 14 to 18% by weight, in each case based on the total weight of the solution S.

In another preferred embodiment, the solution S comprises 3,4-dimethyl-1H-pyrazole (DMP) in an amount of from 60 to 68% by weight, preferably from 62 to 66% by weight, in each case based on the total weight of the solution S.

In another preferred embodiment, the solution S comprises water in an amount of from 14 to 26% by weight, preferably from 16 to 24% by weight, more preferably from 18 to 22% by weight, in each case based on the total weight of the solution S.

In a preferred embodiment, the solution S, which is used as a precursor for preparing the formulation F in the process of the present invention, comprises
- from 14 to 18% by weight of 3,4-dimethyl-1H-pyrazole phosphate,
- from 62 to 66% by weight of 3,4-dimethyl-1H-pyrazole, and
- from 18 to 22% by weight of water,
in each case based on the total weight of the solution S.

In a more preferred embodiment, the solution S comprises
- about 16% by weight of 3,4-dimethyl-1H-pyrazole phosphate,
- about 64% by weight of 3,4-dimethyl-1H-pyrazole, and
- about 30% by weight of water,
in each case based on the total weight of the solution S.

In connection with the above embodiment, the term "about" refers to a variance of ±0.5, preferably ±0.2.

In a preferred embodiment of the process of the invention, from 20 to 30% by weight of the solution S, from 15 to 25% by weight of water and from 40 to 60% by weight of phosphoric acid are mixed with each other in the mixing step, in each case based on the total amount of the resulting mixture. It is to be understood that the amounts of water and phosphoric acid are selected such that the desired weight percent amounts of formulation F are obtained.

In a more preferred embodiment, mixing of solution S with water and phosphoric acid is performed by adding the solution S to a mixture of water and phosphoric acid.

Advantageously, no heating step is required in order to obtain formulation F in the form of a solution, i.e. being visually free from DMPP crystals.

In a preferred embodiment of the process of the invention, the step of mixing the solution S with water and phosphoric acid is performed without applying heat.

It is to be understood that the process of the present invention may also comprise the preparation of solution S.

In one preferred embodiment, the process therefore further comprises the step of preparing the solution S by adding 3,4-dimethyl-1H-pyrazole to a mixture comprising phosphoric acid and water at a temperature of from 30° C. to 80° C., wherein
- 3,4-dimethyl-1H-pyrazole is provided in an amount of from 63 to 81% by weight,
- phosphoric acid is provided in an amount of from 5 to 11% by weight, and
- water is provided in an amount of from 10 to 30% by weight,
in each case based on the total weight of the resulting solution S.

It is to be understood that the temperature of from 30° C. to 80° C. does not have to be applied over the whole step of adding the 3,4-dimethyl-1H-pyrazole (DMP) to the mixture comprising phosphoric acid and water. Instead, a first portion of DMP may be added at temperatures below 30° C., e.g. at 20-25° C., which results in the precipitation of DMPP, and then the mixture may be heated to a temperature of from 30° C. to 80° C., so as to obtain a solution, and then the residual amount of DMP may be added.

Preferably, the temperature is from 40° C. to 70° C., more preferably from 50° C. to 65° C.

In another embodiment, the present invention relates to a formulation F comprising
- from 10 to 50% by weight of 3,4-dimethyl-1H-pyrazole phosphate,
- from 30 to 50% by weight of phosphoric acid, and
- from 10 to 60% by weight of water,
in each case based on the total weight of formulation F, which is obtainable by the process according to the present invention.

The formulation F is advantageous in terms of the cold stability, which can be attributed to the process of preparing the formulation F according to the invention. Preferably, crystallization of 3,4-dimethyl-1H-pyrazole phosphate (DMPP) only occurs below 20° C.

In one preferred embodiment, the formulation F comprises 3,4-dimethyl-1H-pyrazole phosphate (DMPP) in an amount of from 25 to 45% by weight, more preferably in an amount of from 28 to 42% by weight, most preferably in an amount of from 30 to 40% by weight, particularly preferably in an amount of from 32 to 38% by weight, particularly more preferably in an amount of from 33 to 37% by weight, particularly most preferably in an amount of from 34 to 36% by weight, in each case based on the total weight of the formulation F.

In another preferred embodiment, the formulation F comprises phosphoric acid in an amount of from 15 to 45% by weight, more preferably in an amount of from 25 to 45% by weight, most preferably in an amount of from 30 to 45% by weight, particularly preferably in an amount of from 35 to 45% by weight, particularly more preferably in an amount of from 36 to 42% by weight, particularly most preferably in an amount of from 37 to 39% by weight, in each case based on the total weight of the formulation F.

In another preferred embodiment, the formulation F comprises water in an amount of from 20 to 50% by weight, more preferably from 20 to 40% by weight, most preferably from 27 to 29% by weight, in each case based on the total weight of the formulation F.

In a preferred embodiment, formulation F comprises
from 30 to 40% by weight of 3,4-dimethyl-1H-pyrazole phosphate,
from 35 to 45% by weight of phosphoric acid, and
from 20 to 40% by weight of water,
in each case based on the total weight of formulation F.

In a more preferred embodiment, the formulation F comprises
from 34 to 36% by weight of 3,4-dimethyl-1H-pyrazole phosphate,
from 37 to 39% by weight of phosphoric acid, and
from 27 to 29% by weight of water,
in each case based on the total weight of formulation F.

In an even more preferred embodiment, the formulation F comprises
about 35% by weight of 3,4-dimethyl-1H-pyrazole phosphate,
about 38% by weight of phosphoric acid, and
about 28% by weight of water,
in each case based on the total weight of formulation F.

In connection with the above embodiment, the term "about" refers to a variance of ±0.5, preferably ±0.2.

The formulation F may be advantageously used for treating a fertilizer in order to obtain a fertilizer-nitrification inhibitor mixture, which is suitable for fertilizing agricultural soil, while at the same time reducing nitrification.

In one embodiment, the present invention therefore relates to a process for preparing a fertilizer-nitrification inhibitor mixture comprising at least one fertilizer and 3,4-dimethyl-1H-pyrazole phosphate by treating at least one fertilizer with a formulation F as defined herein.

Suitable fertilizers have been define above. Preferably, the fertilizer is a solid or liquid ammonium-containing inorganic fertilizer such as an NPK fertilizer, ammonium nitrate, calcium ammonium nitrate, ammonium sulfate nitrate, ammonium sulfate or ammonium phosphate; a solid or liquid organic fertilizer such as liquid manure, semi-liquid manure, biogas manure, stable manure and straw manure, worm castings, compost, seaweed or guano, or an urea-containing fertilizer such as urea, formaldehyde urea, anhydrous ammonium, urea ammonium nitrate (UAN) solution, urea sulphur, urea based NPK-fertilizers, or urea ammonium sulfate. It is to be understood that also various combinations of fertilizers may be used.

Suitable treatment methods have also been defined above. Preferably, the fertilizer is coated with the formulation F.

In yet another embodiment, the present invention relates to a fertilizer-nitrification inhibitor mixture obtainable by the process for preparing a fertilizer-nitrification inhibitor mixture according to the invention.

In yet another embodiment, the present invention relates to a method of fertilizing agricultural soil by applying at least one fertilizer and a formulation F according to the invention to said soil, or by applying a fertilizer-nitrification inhibitor mixture according to the invention to said soil.

In yet another embodiment, the present invention relates to the use of a formulation F according to the invention for reducing nitrification.

In another embodiment, the present invention relates to the solution S as described above, which is a valuable precursor for preparing the formulation F according to the invention, wherein the solution S comprises
from 10 to 22% by weight of 3,4-dimethyl-1H-pyrazole phosphate,
from 58 to 70% by weight of 3,4-dimethyl-1H-pyrazole, and
from 10 to 30% by weight of water,
in each case based on the total weight of the solution S.

In one preferred embodiment, the solution S comprises 3,4-dimehtyl-1H-pyrazole phosphate (DMPP) in an amount of from 12 to 20% by weight, preferably from 14 to 18% by weight, in each case based on the total weight of the solution S.

In another preferred embodiment, the solution S comprises 3,4-dimethyl-1H-pyrazole (DMP) in an amount of from 60 to 68% by weight, preferably from 62 to 66% by weight, in each case based on the total weight of the solution S.

In another preferred embodiment, the solution S comprises water in an amount of from 14 to 26% by weight, preferably from 16 to 24% by weight, more preferably from 18 to 22% by weight, in each case based on the total weight of the solution S.

In a preferred embodiment, the solution S comprises
from 14 to 18% by weight of 3,4-dimethyl-1H-pyrazole phosphate,
from 62 to 66% by weight of 3,4-dimethyl-1H-pyrazole, and
from 18 to 22% by weight of water,
in each case based on the total weight of the solution S.

In a more preferred embodiment, the solution S comprises
about 16% by weight of 3,4-dimethyl-1H-pyrazole phosphate,
about 64% by weight of 3,4-dimethyl-1H-pyrazole, and
about 30% by weight of water,
in each case based on the total weight of the solution S.

In connection with the above embodiment, the term "about" refers to a variance of ±0.5, preferably ±0.2.

The solution S is suitable for use in the preparation of the formulation F according to the present invention.

In another embodiment, the present invention relates to a process for preparing the solution S as defined above by adding 3,4-dimethyl-1H-pyrazole to a mixture comprising phosphoric acid and water at a temperature of from 30° C. to 80° C., wherein
3,4-dimethyl-1H-pyrazole is provided in an amount of from 63 to 81% by weight,
phosphoric acid is provided in an amount of from 5 to 11% by weight, and
water is provided in an amount of from 10 to 30% by weight,
in each case based on the total weight of the resulting solution S.

It is to be understood that the temperature of from 30° C. to 80° C. does not have to be applied over the whole step of adding the 3,4-dimethyl-1H-pyrazole (DMP) to the mixture comprising phosphoric acid and water. Instead, a first portion of DMP may be added at temperatures below 30° C., e.g. at 20-25° C., which results in the precipitation of DMPP, and then the mixture may be heated to a temperature of from 30° C. to 80° C., so as to obtain a solution, and then the residual amount of DMP may be added.

Preferably, the temperature is from 40° C. to 70° C., more preferably from 50° C. to 65° C.

In yet another embodiment, the present invention relates to a solution S obtainable by the process for preparing the solution S defined above.

The present invention is further illustrated by the following examples.

EXAMPLES

Example 1

Preparation of a solution S1 comprising about 16% by weight of 3,4-dimethyl-1H-pyrazole phosphate (DMPP), about 64% by weight of 3,4-dimethyl-1H-pyrazole (DMP) and about 30% by weight of water, based on the total weight of the solution S1.

The following amounts according to Table 1 were used.

TABLE 1

| | Amount [% by weight] |
|---|---|
| DMP (a.i.: 98.0%) | 73.45% |
| Orthophosphoric acid (85% in water) | 9.41% |
| Water | Add to 100% |

Water and Orthophosphoric acid ($H_3PO_4$) were charged to a vessel with a heating unit. Crushed DMP was slowly added under stirring, to obtain a white and viscous mixture. The mixture was heated to 60° C. and DMP addition was completed. The viscosity decreased, and a clear, brownish and low viscous solution was obtained.

Example 2

Preparation of a formulation F1 comprising about 35% by weight of 3,4-dimethyl-1H-pyrazole phosphate (DMPP), about 38% by weight of orthophosphoric acid, and about 28% by weight of water, based on the total weight of the formulation F1 using solution S1

The following amounts according to Table 2 were used.

TABLE 2

| | Amount [% by weight] |
|---|---|
| Solution S1 (DMPP: 16%, DMP: 64%) | 24.17% |
| Orthophosphoric acid (85% in water) | 55.65% |
| Water | Add to 100% |

Water and Orthophosphoric acid ($H_3PO_4$) were charged to a vessel with a heating unit. Solution S1 was added. The temperature increases due to neutralization enthalpy so that in general no additional heating is required. A light turbid solution of DMPP was obtained.

Cold stability was tested as follows: Samples of the formulation F1 were put on storage at different temperatures for 1 week. Then traces of DMPP seeding crystals were added and the mixture was stored for another week at the same temperature. Then, the samples were visually investigated for crystals.

It was observed that formulation F1 only crystallized below 20° C. When the crystallized solution is slowly heated it becomes a clear solution at approx. 25° C.

Comparative Example 3

Preparation of formulation F2 comprising about 35% by weight of 3,4-dimethyl-1H-pyrazole phosphate (DMPP), about 38% by weight of orthophosphoric acid, and about 28% by weight of water, based on the total weight of the formulation F2 starting from crystalline DM PP.

The following amounts according to Table 3 were used.

TABLE 3

| | Amount [% by weight] |
|---|---|
| DMPP (a.i.: 98.4%) | 35.73% |
| Orthophosphoric acid (85% in water) | 44.19% |
| Water | Add to 100% |

Water and Orthophosphoric acid ($H_3PO_4$) were charged to a vessel with a heating unit. DMPP was added under stirring and dissolved. Heating to 60° C. was required for complete dissolution of DMPP. A clear solution of DMPP was obtained, which crystallized below 30° C.

Cold stability was tested as described in Example 2.

It was observed that formulation F2 crystallized already below 30° C. When the crystallized solution is slowly heated it becomes a clear solution at approx. 40° C.

The invention claimed is:

1. A process for preparing a formulation F for reducing nitrification, said formulation F comprising:
    from 10 to 50% by weight of 3,4-dimethyl-1H-pyrazole phosphate,
    from 10 to 50% by weight of phosphoric acid, and
    from 10 to 60% by weight of water,
    in each case based on the total weight of formulation F, wherein the process for preparing the formulation F comprises the step of mixing
    (a) a solution S comprising:
        from 10 to 22% by weight of 3,4-dimethyl-1H-pyrazole phosphate,
        from 58 to 70% by weight of 3,4-dimethyl-1H-pyrazole, and
        from 10 to 30% by weight of water,
        in each case based on the total weight of the solution S, with
    (b) water and phosphoric acid, so as to prepare said formulation F.

2. The process according to claim 1, wherein the formulation F comprises:
    from 10 to 50% by weight of 3,4-dimethyl-1H-pyrazole phosphate,
    from 30 to 50% by weight of phosphoric acid, and
    from 10 to 60% by weight of water,
    in each case based on the total weight of the formulation F.

3. The process according to claim 2, wherein the formulation F comprises:
    from 30 to 40% by weight of 3,4-dimethyl-1H-pyrazole phosphate,
    from 35 to 45% by weight of phosphoric acid, and
    from 20 to 40% by weight of water,
    in each case based on the total weight of the formulation F.

4. The process according to claim 3 further comprising:
    preparing a fertilizer-nitrification inhibitor mixture comprising at least one fertilizer and 3,4-dimethyl-1H-pyrazole phosphate by treating at least one fertilizer with the formulation F.

5. The process according to claim 3 further comprising:
    fertilizing agricultural soil by applying at least one fertilizer and the formulation F.

6. The process according to claim 2 further comprising:
preparing a fertilizer-nitrification inhibitor mixture comprising at least one fertilizer and 3,4-dimethyl-1H-pyrazole phosphate by treating the at least one fertilizer with the formulation F.

7. The process according to claim 6 further comprising:
fertilizing agricultural soil by applying the fertilizer-nitrification inhibitor mixture to said soil.

8. The process according to claim 2 further comprising:
fertilizing agricultural soil by applying at least one fertilizer and the formulation F.

9. The process according to claim 1, wherein from 20 to 30% by weight of the solution S, from 15 to 25% by weight of water and from 40 to 60% by weight of phosphoric acid are mixed with each other in the mixing step, in each case based on the total amount of the resulting mixture.

10. The process according to claim 9, wherein mixing of solution S with water and phosphoric acid is performed by adding the solution S to a mixture of water and phosphoric acid.

11. The process according to claim 1, wherein formulation F comprises:
from 30 to 40% by weight of 3,4-dimethyl-1H-pyrazole phosphate,
from 35 to 45% by weight of phosphoric acid, and
from 20 to 40% by weight of water,
in each case based on the total weight of formulation F.

12. The process according to claim 1, wherein the solution S comprises:
from 14 to 18% by weight of 3,4-dimethyl-1H-pyrazole phosphate,
from 62 to 66% by weight of 3,4-dimethyl-1H-pyrazole, and
from 18 to 22% by weight of water,
in each case based on the total weight of the solution S.

13. The process according to claim 1, wherein the step of mixing the solution S with water and phosphoric acid is performed without applying heat.

14. The process according to claim 1, wherein the process further comprises the step of preparing the solution S by adding 3,4-dimethyl-1H-pyrazole to a mixture comprising phosphoric acid and water at a temperature of from 30° C. to 80° C., wherein
3,4-dimethyl-1H-pyrazole is provided in an amount of from 63 to 81% by weight,
phosphoric acid is provided in an amount of from 5 to 11% by weight, and
water is provided in an amount of from 10 to 30% by weight,
in each case based on the total weight of the resulting solution S.

15. A solution S comprising:
from 10 to 22% by weight of 3,4-dimethyl-1H-pyrazole phosphate,
from 58 to 70% by weight of 3,4-dimethyl-1H-pyrazole, and
from 10 to 30% by weight of water,
in each case based on the total weight of the solution S, wherein the solution S is a precursor for preparing the formulation F as defined in claim 2.

16. A process for preparing the solution S as defined in claim 15 by adding 3,4-dimethyl-1H-pyrazole to a mixture comprising phosphoric acid and water at a temperature of from 30° C. to 80° C., wherein
3,4-dimethyl-1H-pyrazole is provided in an amount of from 63 to 81% by weight,
phosphoric acid is provided in an amount of from 5 to 11% by weight, and
water is provided in an amount of from 10 to 30% by weight,
in each case based on the total weight of the resulting solution S.

17. A solution S obtained by the process according to claim 16.

18. The solution S according to claim 15 comprising:
from 14 to 18% by weight of 3,4-dimethyl-1H-pyrazole phosphate,
from 62 to 66% by weight of 3,4-dimethyl-1H-pyrazole, and
from 18 to 22% by weight of water,
in each case based on the total weight of the solution S.

* * * * *